US010578468B2

(12) United States Patent
Breton

(10) Patent No.: US 10,578,468 B2
(45) Date of Patent: Mar. 3, 2020

(54) REAL-TIME FLUID SPECIES MASS FLOWMETER

(71) Applicant: Leo Breton, Washington, DC (US)

(72) Inventor: Leo Breton, Washington, DC (US)

( * ) Notice: Subject to any disclaimer, the term of this patent is extended or adjusted under 35 U.S.C. 154(b) by 0 days.

(21) Appl. No.: 15/430,492

(22) Filed: Feb. 12, 2017

(65) Prior Publication Data

US 2017/0234707 A1 Aug. 17, 2017

Related U.S. Application Data

(60) Provisional application No. 62/294,956, filed on Feb. 12, 2016.

(51) Int. Cl.
*G01N 33/00* (2006.01)
*G01F 1/46* (2006.01)

(52) U.S. Cl.
CPC ............ *G01F 1/46* (2013.01); *F01N 2560/07* (2013.01); *G01N 33/0036* (2013.01)

(58) Field of Classification Search
CPC .... G01F 1/46; F01N 2560/07; F01N 2560/14; F01N 2560/20; F01N 13/008; G01N 1/2252
See application file for complete search history.

(56) References Cited

U.S. PATENT DOCUMENTS

| | | | | | |
|---|---|---|---|---|---|
| 5,571,946 | A | * | 11/1996 | Koshi | G01N 1/2258 73/28.01 |
| 6,148,656 | A | * | 11/2000 | Breton | F01N 13/008 73/114.71 |
| 6,382,014 | B1 | * | 5/2002 | Breton | F01N 13/008 73/114.76 |
| 6,439,027 | B1 | * | 8/2002 | Hiss, III | G01N 1/2258 422/88 |
| 6,470,732 | B1 | * | 10/2002 | Breton | F01N 13/008 73/114.69 |
| 9,000,374 | B2 | * | 4/2015 | Parks, II | G01N 21/59 250/339.06 |
| 9,068,933 | B2 | * | 6/2015 | Parks, II | G01N 21/3504 |
| 2002/0108451 | A1 | * | 8/2002 | May | G01F 1/44 73/861.63 |
| 2009/0223309 | A1 | * | 9/2009 | Kurz | G01F 1/46 73/863.03 |
| 2010/0292934 | A1 | * | 11/2010 | Stark | G01F 1/363 702/24 |
| 2011/0285998 | A1 | * | 11/2011 | Hara | G01N 21/3504 356/437 |

* cited by examiner

*Primary Examiner* — Harshad R Patel

(57) ABSTRACT

A chemical species mass flow meter measurement system for use in fluid mixture streams includes a chemical species concentration detection analyzer physically located within a fluid volume flow rate sensing probe along with bulk temperature and pressure sensing devices for relating to standard conditions. The system uses concentration detection analyzers specifically suited to the intended application. Applications include the measurement of exhaust mass emissions from vehicles, the fuel economy of vehicles, as well as the measurement of the mass flow rate of chemical species of interest in general industrial processes.

9 Claims, 4 Drawing Sheets

REAL-TIME FLUID SPECIES MASS FLOWMETER

CROSS-REFERENCE TO RELATED APPLICATIONS

Not Applicable

STATEMENT REGARDING FEDERALLY SPONSORED RESEARCH OR DEVELOPMENT

This invention was not made with federal funding or resources.

REFERENCE TO SEQUENCE LISTING, A TABLE, OR A COMPUTER PROGRAM LISTING COMPACT DISK APPENDIX

Not Applicable

BACKGROUND OF THE INVENTION

The present invention is in the technical field of mass flow measurement of the constituent chemical species of a flowing fluid mixture. It relates to a system and a method for real-time sensing and recording of the mass flow rates of the individual components of interest of a fluid mixture flowing in a pipe or other conduit. More specifically, the invention relates to a multi-species mass flow rate measurement system which can be inserted in a fluid stream to provide output signals indicative of the fluid species mass flow rates and a method of determining the mass flow rates of each of the detected species of interest from the species concentration detector and bulk fluid stream flow rate detector comprising the system. The invention has broad applicability to industrial processes and the measurement of pollutants in vehicle exhaust gas.

It is desirable to accurately measure the mass flow rates of the constituent species of fluid streams in many industrial processes and for environmental compliance testing purposes. But it is well-known that under dynamic conditions in which the concentration of species of interest and the fluid flow rate are both changing, there can be a significant error in determining the mass flow rates of the species in the usual manner involving the use of two different devices or probes—one for measuring the concentration of the species of interest and a separate probe, located upstream or downstream from the first probe for determining the bulk fluid flow rate. The error results from a variable time delay due to the inability to continuously synchronize the concentration data series in transient fluid flow with the bulk fluid flow rate data series when the probes are placed apart from each other and from the disturbance of the flow rate signal when the concentration probe is placed in close proximity to the flow measurement probe. Thus there exists the need for an improved mass flow measurement device which is accurate under transient flow conditions in which the concentration of the species of interest is also changing rapidly.

For example, it has been desirable to measure the exhaust gas mass flow rates from internal combustion engines in a laboratory testing setting since the United States Environmental Protection Agency (EPA) began regulating automobile emissions in the 1970s. More recently it has become desirable to measure the exhaust emissions mass flow rates on moving vehicles operated in the real world for regulatory compliance testing purposes [Breton, also the current inventor, U.S. Pat. Nos. 6,148,656; 6,382,014 B1; 6,470,732 B1, henceforth referred to collectively as Breton].

There is also a desire to minimize the effects, e.g. the backpressure created by the measurement devices, on the flow being measured and on the machine or process associated with the flow being measured. Therefore, there is a need for the invention to be practiced in a compact geometrical footprint to minimize the disturbance to the bulk flow, thereby minimizing the effect of the measurement device on the system or machine for which the fluid flow is being measured. For this reason, Breton teaches a mobile emissions measurement system using an exhaust gas flow rate measurement module employing an averaging pitot tube with a narrow cross section. The module is comprised of the pitot tube, a separate pressure sensing means, a separate temperature sensing means, and a gas concentration analyzer sampling port, all permanently mounted in a movable module so that whenever the module is connected to a vehicle tailpipe, it inherently incorporates the necessary upstream and downstream flow diameters needed for accurate flow sensing, even for the worst-case installation expected.

Traditional EPA exhaust emissions compliance testing employs gas and particulate matter analyzers based on specific measurement principles, depending on the chemical species of interest. Because those measurement principles are used by EPA when regulatory compliance or certification testing is done by the Agency, engine and vehicle manufacturers typically use those same analyzers or analyzer technologies to ensure consistency with the regulators' testing results, i.e. there are de facto standard analyzer technologies. For this reason Breton teaches a "Real-Time On-Road Vehicle Exhaust Gas Modular Flowmeter and Emissions Reporting System" in which the exhaust gas analyzers employ the same measurement principles referenced by EPA regulations for each chemical species being measured.

Using the de facto standard analyzer technologies can have a number of drawbacks however, and those drawbacks can be significant for many potential users of a mobile measurement system. For example, the de facto standard gas analyzers must be "warmed up" before use. To ensure accuracy, the standard analyzers must also be calibrated on a regular basis, and "zeroed" and "spanned" prior to each test, requiring the use of numerous, expensive calibration gases of various known concentrations, each contained in a large gas cylinder. Because of these requirements, calibration gases often need to be carried with vehicles being tested.

The traditional analyzers must also be mounted onto or inside the vehicle being tested, requiring a significant volume of space in the vehicle. And some vehicles don't have suitable space for mounting.

Because the concentration signals from remotely mounted gas analyzers are significantly delayed in time compared with the flow rate signals from the flow meter, it is necessary to measure the relative time delay initially and whenever the length of the gas sample hose is changed. Repairs are often necessary because the traditional analyzers draw a sample from the exhaust stream using a pump, check valves, and other plumbing prone to failures.

Parks [U.S. Pat. Nos. 9,000,374 and 9,068,933] teaches a laser-based Exhaust Gas Recirculation (EGR) diagnostic probe for engine research. The probe is capable of measuring the concentration of some gas species. Other chemical species could also be measured by adding additional laser light frequencies to the system. This type of species concentration analyzer with the appropriate frequencies of operation would be desirable for at least one embodiment of the present invention related to exhaust gas mass flow measurement.

Even though Breton teaches how to minimize measurement error by fixing the gas analyzer sampling probe tip in close proximity to the flow sensing means, it is not possible to have them arbitrarily close to each other due to potential disturbance of the exhaust flow profile near the flow sensing means, by the presence of the sampling probe. So the overall accuracy of the traditional measurement system is reduced by a small, variable time shift between the flow rate signal and the gas concentration signal as the engine speed and load change quickly. Breton previously proved that an averaging pitot tube can be highly accurate over large exhaust flow turndown ratios, i.e. large changes in flow rates, and is well suited for vehicle emissions testing because it can be employed with a small geometrical cross-sectional area, minimizing backpressure in the flow to be measured. For testing applications requiring insertion into, or attachment onto a vehicle's tailpipe, the cross-sectional area to flow must be kept as small as possible to prevent the creation of significant backpressure which could alter the operation of the vehicle's engine, thereby affecting the test results. Some vehicles are extremely sensitive to exhaust backpressure because it can interfere with their engine control systems. The minimum averaging pitot tube cross-sectional sizes available commercially are determined by their ability to avoid bending in moving flow streams and their ability to resist process vibrations. It is desirable to avoid using cross-sectional sizes greater than these minimum sizes for exhaust gas measurements on vehicles with narrower tailpipes. Therefore, any alterations of the standard pitot tube probe designs which result in a larger cross-section are undesirable.

It would also be advantageous to possess the ability to continuously measure the exhaust gas mass flow rates of the pollutants of moving vehicles operated in the real world with an embedded measurement system low enough in cost to be able to be permanently installed by vehicle manufacturers on all new vehicles for providing input to a vehicle's on-board diagnostics (OBD) system to indicate the health of the emissions controls, the fuel economy of the vehicle, and for the continuous measurement of the regulatory compliance level of the vehicle over its lifetime. Unfortunately, there are significant manufacturing challenges to making compact devices as described above because increased functionality from a single probe would normally necessitate the use of a larger probe which is disadvantageous because of increased resistance to fluid flow, hence increased backpressure. As stated above, increased exhaust backpressure on a vehicle can alter the vehicle's operation and lead to erroneous test results. Therefore, it is desirable to increase the measurement capabilities of a new species mass flowmeter device that is no larger in cross-section than current, minimum size averaging pitot tubes, while also increasing overall accuracy and ease of use of a larger system based on such devices.

The present invention teaches a mass flow measurement system for constituent gas species in a contained gas flow which eliminates all of the aforementioned drawbacks, thereby increasing the ease of use of the measurement system for the testing of vehicle emissions, as well as the accuracy in measuring fluid species mass flow rates for transient flows and the simplicity and low cost of a mass flow measurement device for high volume applications such as automobiles or numerous industrial applications.

BRIEF SUMMARY OF THE INVENTION

The present mass flowmeter invention solves all of the problems outlined above. It is comprised of a concentration detector or analyzer co-located with a flow measurement detector, ideally in a single probe for insertion into a fluid flowing in a pipe or other conduit. The components, including but not limited to all of the internal structures of the bulk fluid flow measurement means were conceived to be made with conventional machine tools, or optionally to be 3-D printed using additive manufacturing technologies in any suitable material or size, considering the needs dictated by the specific application.

The following description of the present invention teaches how to construct the internal aspects of small cross-sectional area, averaging pitot tubes to create enough open volume for containing, or housing, smaller laser-based and small solid-state fluid species concentration measurement devices, without changing the pitot tube's exterior size or shape, and therefore not changing the differential pressure created and communicated by the pitot tube, for a given flow rate. In this way, co-location of the concentration measurement with the flow measurement can be attained. Co-location of the two detectors in space guarantees the synchronization of the bulk flow rate and concentration signals in time, even with highly compressible and highly transient flows, while preventing the interference of each detector means with the other. Calculating means continuously computes the products of the bulk flow detector, concentration detectors, and the known densities of the fluid species of interest and provides output signals proportional to the mass flow rates of the species of interest under both transient and steady flow conditions.

Optional display means display the calculated mass flow rates of the species of interest, if desired. Separate display and calculating means are not necessary for applications in which the mass flowmeter serves as part of a larger measurement system, e.g. as part of an On-Board Diagnostic (OBD) system provided by a vehicle manufacturer. In that case, the invention provides signal outputs to other input or calculating means used for other vehicle functions.

Choice of the flow measurement principle and the concentration measurement principles depends upon the intended application. In one embodiment for improved EPA regulatory compliance testing purposes as taught by Breton, the flow measurement principle is an averaging pitot tube previously proven by Breton, and subsequently adopted worldwide by the automotive industry, to be suitable for transient exhaust gas flow measurement. An exemplary concentration measurement means taught by Parks is a multi-color, multi-species laser spectroscopy probe suitable, when modified as shown herein, for physically locating within a modified averaging pitot tube such that it does not alter the flow structure created by the averaging pitot tube in the vicinity of the pitot tube sampling ports, yet is in continuous, direct contact with the exhaust gas flow.

In another embodiment for improving the capabilities of OBD systems for new automobiles, a low-cost probe is comprised of a modified averaging pitot tube for flow measurement and a solid-state or electrochemical gas sensor for gas concentration measurement of one or more regulated pollutants related to the health or control of the engine or emissions control system. The flow measurement and gas concentration signals are output to the vehicle or engine control system for use in controlling the engine or emissions controls system and for the detection of undesirable operation of emission control equipment.

Other embodiments are contemplated for industrial and other applications in which the specific flow measurement principle and gas concentration detector operating principles are chosen based on the specific application requirements and cost.

DETAILED DESCRIPTION OF THE INVENTION

Specific embodiments of the present invention for are discussed below. It should be understood that those embodiments are for specific applications for illustrative purposes only and that the present invention has much wider applicability than these or any other single embodiment. Mass flow measurement of chemical species or pollutants of interest contained in fluids comprised of multiple species is widely practiced in many industries and industrial processes. All such processes are contemplated herewith.

Figure 1:
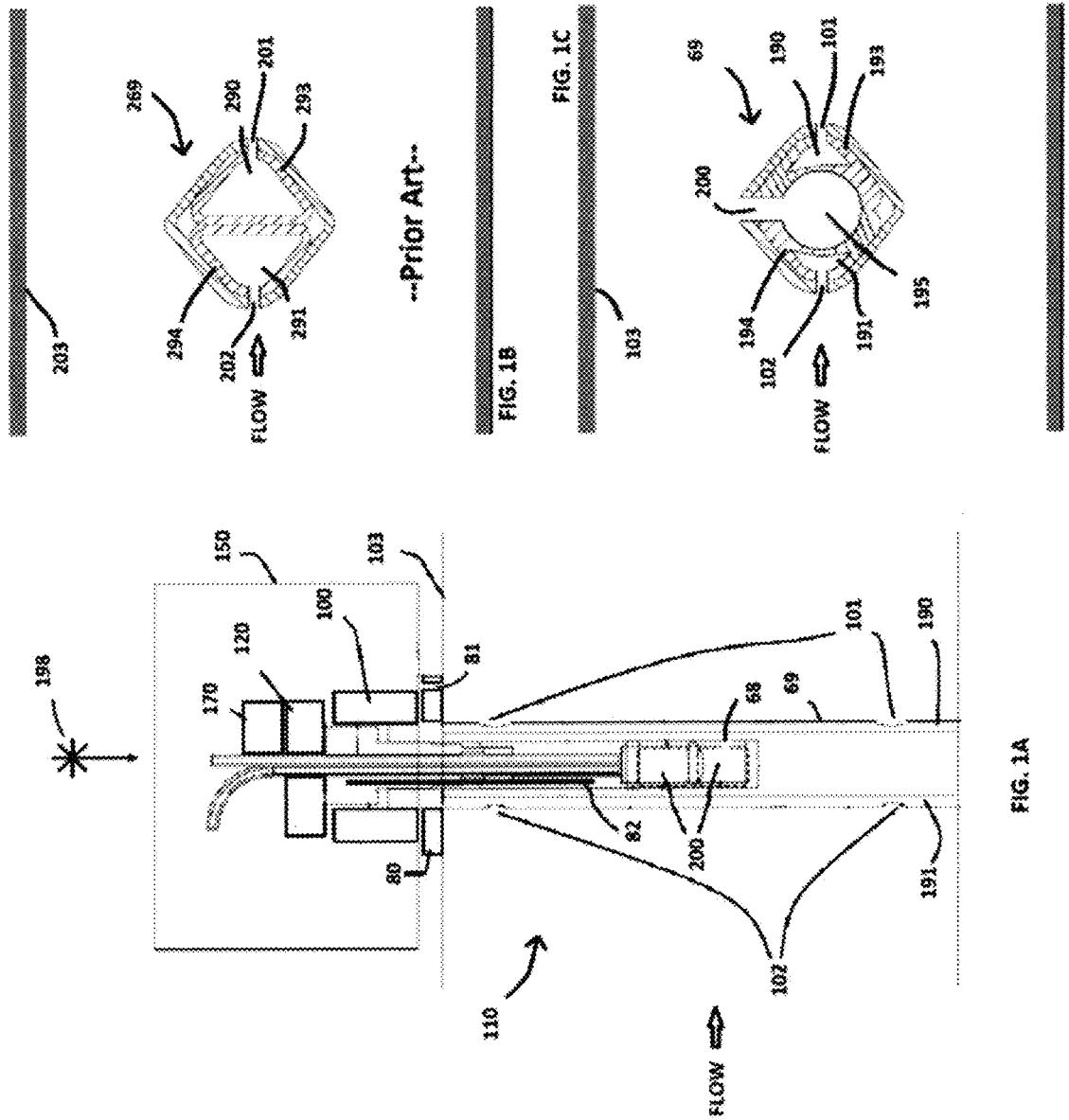
FIG. 1A is a detailed view of an exemplary embodiment of a fluid species mass flow meter for use in measuring the mass flow rate of chemical species in a bulk fluid flow.
FIG. 1B is a view of a cross-section of a typical, commercially available, averaging pitot tube, as installed in a fluid conduit.
FIG. 1C is a view of a cross-section of the mass flow rate probe of FIG. 1A as installed in a fluid conduit (details of the fluid concentration measurement means not shown).

A first exemplary embodiment of the present invention for measuring the mass flow rate of fluid species of interest is shown in FIG. 1A. This embodiment is comprised of a multi species laser-based gas concentration detector 68, constructed as taught by Parks, mounted in lug 80 which has an integral fluid static pressure port 81, communicating static pressure to a pressure transducer 100. The pressure sensed at the static pressure port 81 and the temperature sensed by the thermocouple 82 are used to correct the sensed flow rate to standard conditions.

FIG. 1B is a cross-sectional diagram illustrating the construction of a conventional averaging pitot tube 269, known in the prior art, mounted in a conduit 203, exhibiting upstream sensing port manifold 291 and downstream sensing port manifold 290 formed by upstream enclosure 294 and downstream enclosure 293, the shapes of which are optimized for the associated manufacturing process to make the pitot tube 269. One of the upstream sensing ports 202 and one of the downstream sensing ports 201 are also shown. FIG. 1C shows the construction of a modified averaging pitot tube 69, mounted in a conduit 103, and advantageously constructed to house the laser-based gas concentration detector 68 within the hollow interior 195 formed by employing 3D or additive manufacturing processes in the making of the averaging pitot tube 69. Referring to FIG. 1A, the laser-based gas concentration detector 68, employing at least one frequency of laser light 198, and thermocouple 82 are physically mounted within the averaging pitot tube 69, in the hollow interior 195 created between the upstream sensing port manifold 191 and the downstream sensing port manifold 190, the shape and size of said hollow interior 195 to be formed being dictated by the outer dimensions of the concentration detector 68 and being manufactured as stated above. The upstream sensing port manifold 191 connects all of the upstream pressure sensing ports 102 and the downstream sensing port manifold 190 connects all of the downstream pressure sensing ports 101. The static pressure sensing port 81 can be located in the mounting lug, forming a mass flow measurement probe 110 of minimum cross-sectional area, possessing the same outer dimensions and shape, and producing no more resistance to fluid flow than the unmodified averaging pitot tube 269. The probe 110 is semi-permanently mounted to the process pipe 103 using attachment lug 80.

In one preferred embodiment the averaging pitot tube 69 is constructed of stainless steel using machine tools in a conventional manner. In another preferred embodiment the averaging pitot tube 69 is constructed using a 3-D printing process of stainless steel or other materials, or other additive manufacturing techniques, including the construction of all internal structures and components of the averaging pitot tube 69. For example, the resulting shape of the upstream manifold enclosure material 194 forming the upstream manifold 191, and/or the resulting shape of the downstream manifold material 193 forming the downstream manifold 190, may be very complex and difficult to manufacture using conventional manufacturing methods. The additive manufacturing techniques allow for greater flexibility in combining and integrating a small pitot tube with various other gas concentration, temperature, or pressure sensing components or improved shapes or profiles to cause an increased signal magnitude or greater sensitivity, or for compactness, improved fit, or other possible advantages. In this way, the overall cross-sectional width of the assembly is minimized, thereby minimizing deleterious fluid flow backpressure effects caused by the associated measurements.

The laser-based concentration detector 68 location is displaced longitudinally with respect to the upstream sensing ports 102 and the downstream sensing ports 101, along the averaging pitot tube 69 longitudinal axis to prevent the presence of the detector 68 from disturbing the flow field in the vicinity of the sensing ports 101, 102, thereby preventing the presence of the detector 68 from causing erroneous flow rate measurements by the pitot tube 69. The concentration detector 68 is in communication with the bulk fluid by the provided windows or openings 200 in the pitot tube 69 outer surface and provides an output signal (not shown) indicative of the concentrations $X_1$ through $X_n$ associated with gaseous species of interest 1 through n, respectively, which may be any chosen subset from a set of candidate species including, but not limited to, $CH_4$, $CO$, $CO_2$, $NO$, $NO_2$, or particulate matter number to the calculating means 170.

All supporting and associated electronics and sensors are located in an enclosure 150 physically mounted on top of the measurement probe 110 or in close proximity.

When the novel mass flow measurement probe 110 is installed in a pipe carrying a fluid mixture for an industrial or other process, or alternatively when the measurement probe 110 is installed in a permanently or temporarily attached tube or pipe connected to the exhaust system of a vehicle or engine, it creates a differential pressure which is sensed by the differential pressure sensor 120 indicative of the average exhaust flow velocity in the pipe 103. Flow orifices (not shown) serve to dampen noisy differential pressure signals from reaching the differential pressure sensor 120. Differential pressure sensor 120 outputs a signal to the calculating means 170 indicative of the average fluid flow velocity v in the pipe 103 of known diameter D.

The time delay between the gas concentration detector 68 signal and the corresponding differential pressure sensor 120 output signal is a constant or fixed value equal to zero or nearly equal to zero for any combination of species concentrations and transient flow conditions experienced, because of the co-location of said species concentration detector 68 and averaging pitot tube 69 along the bulk fluid flow path.

The calculating means 170 may be mounted as shown, or may be mounted remotely, as desired for the particular application. Calculating means 170 calculates the mass flow rates (Mdot)$_1$ through (Mdot)n associated with fluid species of interest 1 through fluid species of interest n according to the formula and methodology taught by Breton and provides output signals corresponding to those mass flow rates for interfacing with other devices or for interfacing to a user display device. The mass flow rate M$_i$(t) of a fluid species of interest i is calculated by the calculating means 170 by using the measured bulk fluid volumetric flow rate Q(t) and the measured concentrations Xi(t) of the species of interest i using the known relationships:

$$Q(t)=c*F_{AA}*(h_w)^{1/2}*P^{1/2}(T+273)^{1/2}$$

Where c is a constant which is determined by calibrating with a known bulk fluid flow rate at standard conditions, $F_{AA}$ is a thermal expansion factor to correct for flow area change of the pipe due to varying bulk fluid temperatures as measured by the thermocouple 82, $h_w$ is the pressure difference measured by the differential pressure sensor 120, P is the absolute fluid pressure measured using the pressure port 81, in conjunction with the pressure sensor 100, and T is the fluid bulk temperature as measured by the thermocouple 82, $$\text{And Mdot}_i(t)=k*p_i*X_i(t)*Q(t)$$

Where M$_i$(t) is the mass flow rate of chemical species i, k is a constant dependent on the physical units used, p$_i$ is the know density of the species i, X$_i$ is the measured concentration of chemical species i, and Q(t) is given above.

Figure 2:
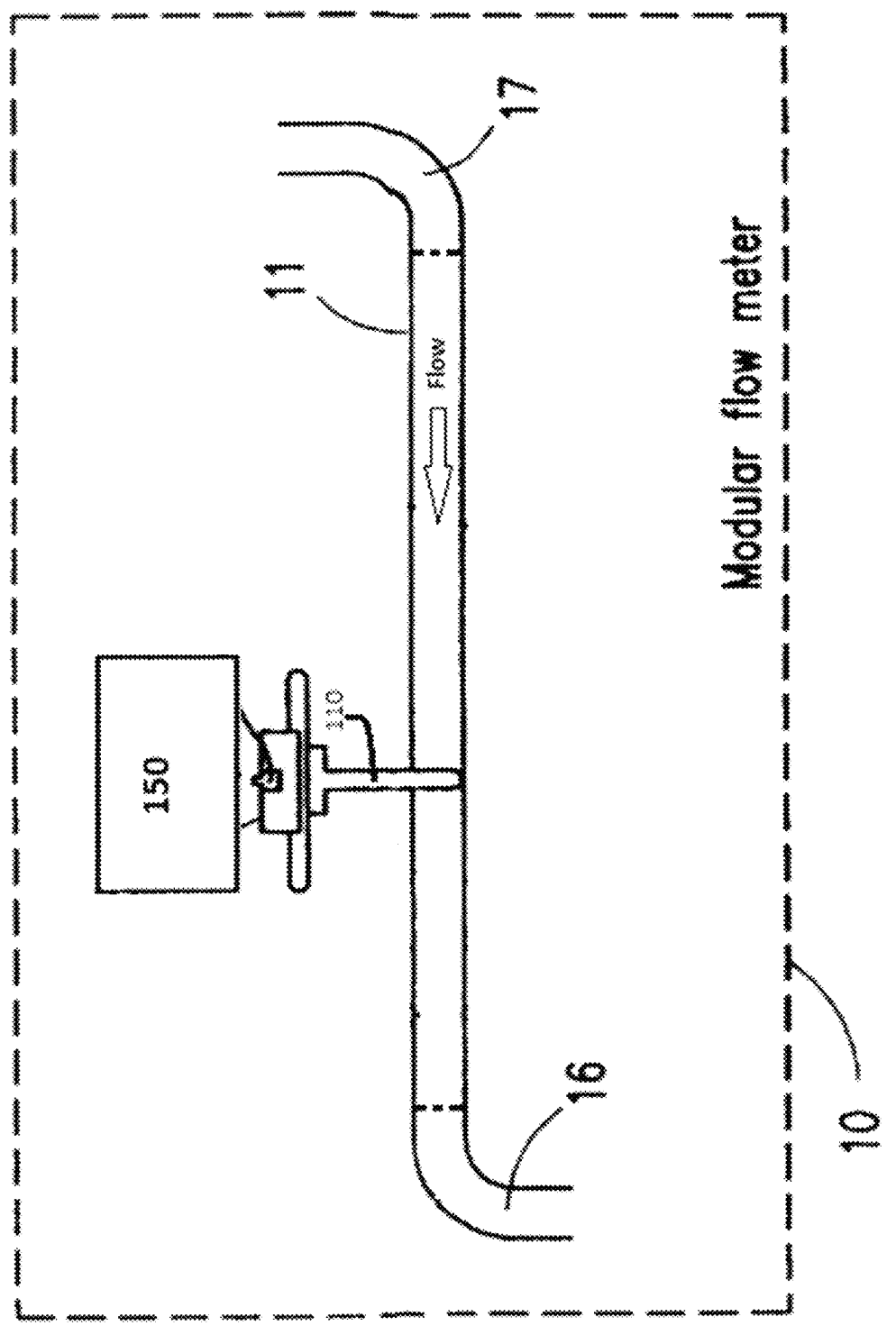
FIG. 2 shows an exemplary embodiment of a portable emissions measurement system employing the fluid species mass flow meter shown in FIG. 1A, for mounting on a passenger vehicle.

FIG. 2 shows an exemplary embodiment of the present invention specifically adapted as a flow meter module 10 for easily mounting the entire species measurement system to the tailpipe of a vehicle and for efficient transfer between different vehicles. This embodiment measures exhaust gas pollutant mass flow rates and has the other advantages taught by Breton, including the optional merging of emissions data with other diagnostic data from other systems and data sources, e.g. scan tools, GPS systems, etc.

A straight pipe section 11 serves as a housing for the flow measurement probe 110 with integral thermocouple 82 and a static pressure transducer 100 (shown in FIG. 1A) using the static pressure port 81. Straight pipe section 11 also serves to provide the requisite straight pipe runs upstream and downstream of the flow measurement probe 110 as taught by Breton. Breton shows pipe elbows 16,17, as shown in FIG. 2 and FIG. 3, are used on most flow meter modules for passenger cars, allowing the flow meter module to be installed close and parallel to the vehicles' bumpers, thereby preventing the module from becoming a hazard to other vehicles.

Figure 3:
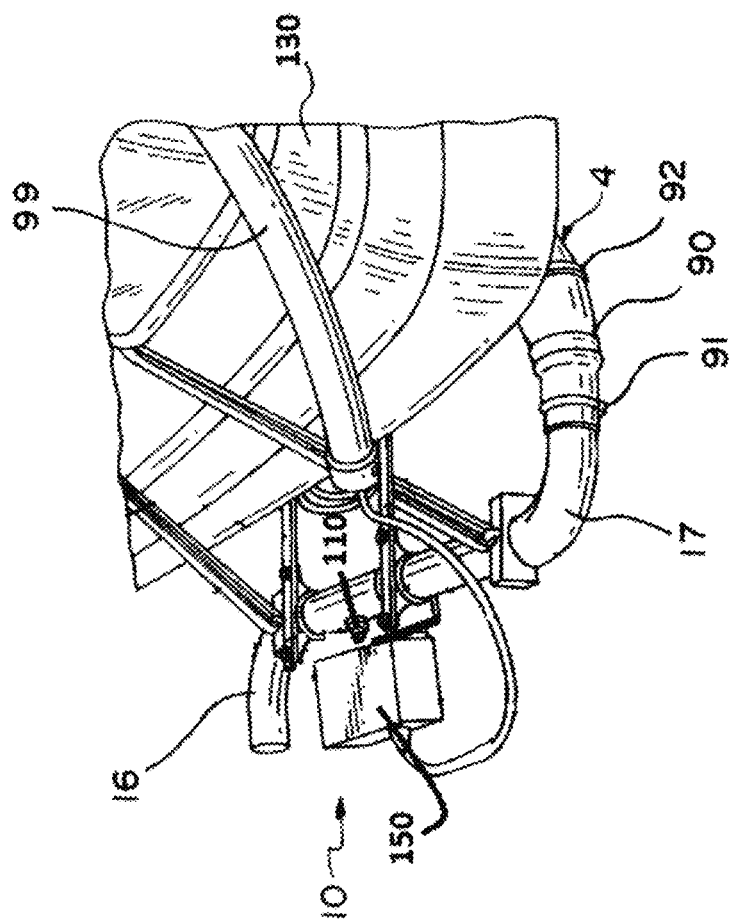
FIG. 3 shows the exemplary embodiment of FIG. 2 installed on a vehicle.

FIG. 3 shows the flow meter module 10 illustrated in FIG. 2 mounted on the rear of a passenger vehicle 130. An example of the connection means for connecting the module 10 of the present invention to the exhaust pipe 4 of vehicle 130 is shown as the elastomeric boot 90 which is connected to the upstream end of elbow 17 of module 10 and to the exhaust pipe 4 by hose clamps 91 and 92. The elastomeric boot may be a high temperature resistant silicone rubber tube of the type used to connect a vehicle exhaust pipe to a conventional (stationary) test stand used in emissions testing. Supporting the flow meter module 10 has already been taught by Breton.

A conduit 99 carries communication means whenever the flow meter module 10 is used as a larger system and needs to communicate with other instruments. Alternatively, wireless communication means can be employed.

Figure 4:
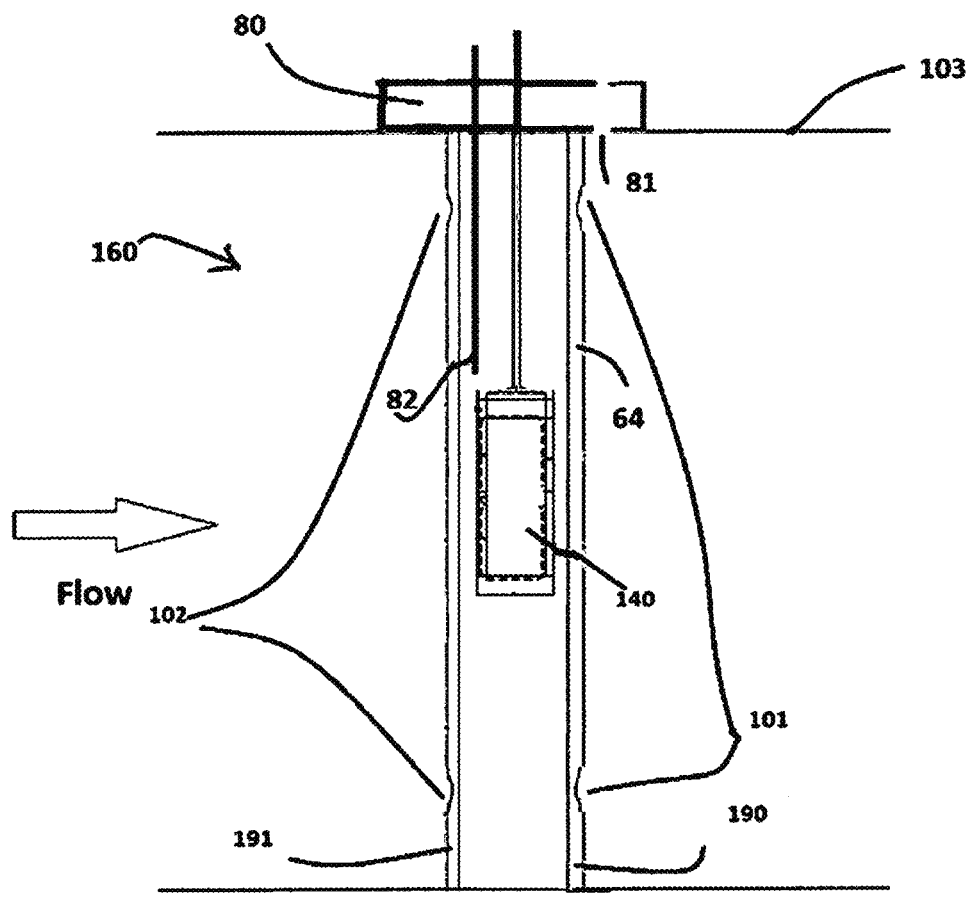
FIG. 4 is a view of an exemplary embodiment of a general industrial chemical species mass flow meter or a vehicle exhaust gas mass flow meter for use in a vehicle monitoring system or On-Board Diagnostics system (OBD).

Referring to FIG. 4, another exemplary embodiment 160 employs a solid state or electrochemical concentration detector 140 substituted for the laser-based detector 68 specified in the earlier exemplary embodiment 110, while maintaining all other features and structures used for calculating chemical species mass flow rates as shown in FIG. 1A. The solid state or electrochemical concentration detector 140 is in direct communication with the surrounding fluid, as enabled by windows or openings located in the pitot tube 64. The shape and space requirements of the specific detector 140 to be employed are considered in the manufacturing process of the averaging pitot tube 64, as described above for the embodiment shown in FIG. 1A. This embodiment may be more suitable for applications where cleaning or servicing of the sensor is not possible or for low-cost, high production volume applications of the invention, for example as an original equipment component included on new vehicles or engines for the purpose of On-Board Diagnostics (OBD) sensing and reporting on vehicles, feedback or other control of engine emissions controls, or exhaust emissions compliance reporting which may be desired or contemplated in future government regulations, including but not limited to transponder-based reporting from operating vehicles to remote data collection locations.

Other potential applications include the measurement of the mass flow of chemical species of interest in industrial fluid flows, e.g. in manufacturing plants and oil refineries.

Alternatively, or in addition to providing said output signals, the calculating means (not shown) optionally provides output signals to the display (not shown) for the purpose of displaying the mass flow rates of said fluid species of interest.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A chemical species flow rate measurement probe for insertion into a fluid flowing in a conduit, comprising:
   a pitot tube flowmeter probe comprising separate high pressure and low pressure sensing ports and a hollow interior having an opening suitable for co-locating a fluid chemical species concentration detector;
   a fluid chemical species concentration detector for detecting the concentration of at least one fluid species and outputting signals indicative of each detected species concentration,
   said fluid chemical species concentration detector detects the concentrations of the at least one fluid species from said hollow interior of the pitot tube flowmeter probe.

2. The chemical species flow rate measurement probe according to claim 1, wherein the hollow interior is not in fluid communication with the high pressure or the low pressure sensing ports.

3. The chemical species flow rate measurement probe according to claim 1, wherein the fluid chemical species concentration detector comprises at least one laser-based gas concentration detector for spectroscopic analysis of the concentrations of at least one chemical species.

4. The chemical species flow rate measurement probe according to claim 1, wherein the fluid chemical species concentration detector comprises at least one solid-state or electrochemical concentration detector for analysis of the concentrations of the at least one chemical species.

5. The chemical species flow rate measurement probe according to claim 1, further comprising a differential pressure sensor arranged to measure a pressure difference between the pitot tube flowmeter probe high pressure sensing port, the low pressure sensing port, and output a signal indicative of the measured pressure difference.

6. The chemical species flow rate measurement probe according to claim 5, further comprising a temperature sensor located within the hollow interior of the pitot tube flowmeter probe for sensing a temperature of the fluid within the hollow interior and outputting a signal indicative of the temperature.

7. The chemical species flow rate measurement probe according to claim 6, further comprising:
   a pressure transducer for sensing a pressure of the fluid and outputting a signal indicative of the pressure; and
   a static pressure port for communicating the pressure to the pressure transducer.

8. A chemical species mass flow rate measurement system comprising:
   the chemical species flow rate measurement probe according to claim 7; and
   a computing device for calculating the mass flow rate of at least one chemical species of a fluid based on the differential pressure sensor signal, the temperature sensor signal, the pressure transducer signal, and the signals indicative of each detected species concentration.

9. A method for measuring the steady-state and transient mass flow rates of at least one chemical species comprising a fluid flowing in a conduit, comprising:
   measuring a bulk flow rate of the fluid with a pitot tube flowmeter probe which comprises a hollow interior for co-locating a fluid chemical species concentration detector;
   measuring a temperature and a pressure of the fluid;
   calculating a corrected bulk flow rate of the fluid based on the measured temperature and pressure;
   measuring the concentration of at least one fluid chemical species using a fluid chemical species concentration detector located inside the hollow interior of the pitot tube flow meter probe; and
   calculating the mass flow rate of the at least one fluid chemical species based on the corrected bulk flow rate of the fluid and the measured concentrations of the at least one fluid chemical species.

* * * * *